(12) United States Patent
Wei (10) Patent No.: US 9,956,232 B2
(45) Date of Patent: May 1, 2018

(54) DIALKYL-PHOSPHINOYL-ALKANE (DAPA) COMPOUNDS AND COMPOSITIONS FOR TREATMENT OF LOWER GASTROINTESTINAL TRACT DISORDERS

(71) Applicant: Edward Tak Wei, Berkeley (CA)

(72) Inventor: Edward Tak Wei, Berkeley (CA)

( * ) Notice: Subject to any disclaimer, the term of this patent is extended or adjusted under 35 U.S.C. 154(b) by 63 days.

(21) Appl. No.: 14/998,458

(22) Filed: Jan. 6, 2016

(65) Prior Publication Data
US 2017/0189428 A1    Jul. 6, 2017

(51) Int. Cl.
*A61K 31/66* (2006.01)
*A61K 9/00* (2006.01)
*A61K 47/02* (2006.01)

(52) U.S. Cl.
CPC ............ *A61K 31/66* (2013.01); *A61K 9/0031* (2013.01); *A61K 9/0053* (2013.01); *A61K 47/02* (2013.01)

(58) Field of Classification Search
CPC ...... A61K 31/66; A61K 47/02; A61K 9/0053; A61K 9/0031
See application file for complete search history.

(56) References Cited

U.S. PATENT DOCUMENTS 4,070,496 A    1/1978 Rowsell

OTHER PUBLICATIONS

Amato. Effects of methol on circular smooth muscle of human colon: the mechanism of action. (2014) Eur J Pharmacol. 740: 295-301. [061, In 2].
Behrendt. 2004. cold-menthol receptor TRPM8 and vanilloid receptor type-1 VR1 using a flurometric imaging plate reader brit Pharmacol. 141: 737, 2004. [011, In 8].
Birrell. TrpA1 agonists evoke coughing in human volunteers. Amer. J. respiratory and critical care medicine 180, 1042-7, 2009. [056, In 2].
Bressler. Clinical guidelines for the medical management of nonhospitalized ulcerative colitis: the Toronto consensus, Gastro148, 1035-1058 (2015) [034, In 17].
Defalco et al. 5-benzyloxytryptamine as an antagonist of TRPM8., Bioorg. Med. Chem. Lett. 20, 7076-9 (2010). [045, In 10].
DeJong TRPM8 on mucosal sensory nerves regulates colitogenic responses by innate immune cells via CGRP. Mucosal. Immunol. 8: 491-504, 2015 [009, In 20].
Dickerson., Wet mammals shake at tune frequencies to dry. J.R. Soc. Interface 9: 3208-3218, 2012 [075, In 2].
Hosoya. 2014. TRPM8 has a key role in experimental colitis-induced visceral hyperalgesia in mice. Neurogastro.Motil. 26, 1112-21 [009, In 12].
Kappleman. Recent trends in the prevalence of Crohn's disease and ulcerative colitis in a commercially insured US population., Dig. Dis. Sci. 58, 519-25 (2013) [030, In 5].
McKemy. 2002. Identification of a cold receptor reveals a general role for TRP channels in thermosensation. Nature 416, 52-8. [062, In 12].
Nair. 2001. safety assessment of Mentha Piperita (Peppermint) Oil, Mentha Piperita (Peppermint) Leaf Extract, Mentha Piperita (Peppermint) Leaf, [044, In 4].
Odes. 2008. How expensive is inflammatory bowel disease? A critical analysis. World J. Gastroenterol. 14, 6641-6647. [026, In 22].
Ortega-Jimenez, Aerial shaking performance of we Anna's hummingbirds. J.R. Soc. Interface 9: 1093-1099, 2012. [075, In 3].
Patel. Inhibition of sensory nerve activity and the cough reflex in guinea-pigs by cannabinoid (CB2) receptor activation. Brit. J. Pharm. 140: 261, 2003.[056, In3].
Penuelas. 2007. Contractile effect of TRPA1 receptor agonists in the isolated mouse intestine. Eur. J. Pharmacol. 576, 143-50. [009, In 10].
Ramachandran. TRPM8 attenuates inflammatory responses in mouse models of colitis. Proc. Natl. Acad. Sci. U. S. A. 110, 7476-81, 2013 [009, In 18].
Reed. Transcapillary exchange: importance of the interstitial fluid pressure and the extracellular matrix. Cardiovascular Res. 87: 211-217, 2010. [069, In 2].
Sandborn. Oral 5-ASA therapy in ulcerative colitis: what are the implications of the new formulations?, J. Clin. Gastroenterol. 42, 338-44 (2008). [035, In 13].
Siddall. Simplified preparation of some trisubstituted phosphine oxides. J. Chemical Engineering Data 10: 303-305, 1965 [021, In 23].
Watson. Compounds with the Menthol Cooling Effect. J. Soc. Cosmet. Chem. 29: 185-200, 1978 [011, In 1].
Wei. Sensory/cooling agents for skin discomfort. Journal Skin Barrier Res 14: 5-12, 2012). [045, In 3].

(Continued)

*Primary Examiner* — Sudhakar Katakam (57) ABSTRACT

Heat abstraction from the body's surfaces causes sensations of cold from the skin, orbit, nose, mouth, throat, upper esophagus, airways, and anogenital surfaces. The detection of heat abstraction at these sites is via TRPM8, a neuronal protein linked to nerve membranes. Chemical agents that act on TRPM8 can also produce sensations of cold, but the surface of the lower gastrointestinal tract (LGIT) does not "feel cold", yet it contains cells with TRPM8. The pharmacology of TRPM8 in the LGIT is an unexplored subject. Menthol has a relaxant effect on gut smooth muscle, but this action is not via TRPM8. Here, a class of selective TRPM8 agonists, called 1-Dialkyl-phosphinoyl-alkanes (Dapa) were synthesized, and the potency and selectivity on TRP channels were characterized. Certain Dapa molecules were shown to inhibit neural signals in isolated vagus nerve and to exert anti-inflammatory effects in a model of heat-injury. When applied to the human colon muscle, a Dapa embodiment inhibited contractions with a median inhibitory concentration of 8 µg/mL. Methods for coating and formulation of Dapa with excipients for delivery to the colonic mucosa are described. The preferred Dapa embodiments are believed useful in treating the muscle spasms and the inflammation of LGIT dysfunction.

14 Claims, 5 Drawing Sheets

(56) References Cited

OTHER PUBLICATIONS

Wei., Anti-inflammatory peptide agonists. Annual Review Pharmacol Toxicol. 33:9-108, 1993. [066, In 10].
Wei. Pharmacological aspects of shaking behavior producted by TRH, AG-3-5, and morphine withdrawal. Fed.Proc. 40: 1491-1496, 1981 [075, In3].
Wirtz. Chemically induced mouse models of intestinal inflammation. Nature Protocols, Jun. 1, 2017. [071, In3].
Yang. Colon-specific drug delivery: New approaches and in vitro/in vivo evaluation, Int. J. Pharm. 2351-15.(2002).[034, In 5].

DIALKYL-PHOSPHINOYL-ALKANE (DAPA) COMPOUNDS AND COMPOSITIONS FOR TREATMENT OF LOWER GASTROINTESTINAL TRACT DISORDERS

CROSS-REFERENCE TO RELATED APPLICATIONS

This application is a continuation-in-part of International (PCT) Patent Application No PCT/GB2013/052750, filed Oct. 22, 2013 and International (PCT) Patent Application No PCT/GB2013/052751, filed Oct. 22, 2013, U.S. Ser. No. 14/544,042 filed Nov. 18, 2014, U.S. Ser. No. 14/544,355 filed Dec. 29, 2014, and U.S. Ser. No. 14/545,014 filed Mar. 16, 2015.

TECHNICAL FIELD

The present discovery pertains generally to the field of therapeutic compounds. More specifically the present discovery pertains to a set of dialkyl-phosphinoyl-alkane molecules [Dapa] that are believed useful to treat (e.g., suppress) dysfunction, e.g. spasms and inflammation, originating from the walls of the lower gastrointestinal tract [LGIT]. This invention more particularly relates to therapeutic compositions formulated for delivery to the luminal surfaces of the human LGIT. The present discovery pertains to Dapa that inhibit contractility of the human colonic muscle, hence exerting an anti-spasmodic action. The preferred embodiments are pharmaceutical compositions formulated for delivery to the enteric mucosa as a tablet or capsule for oral intake, or as a suppository for rectal administration, to facilitate delivery of such Dapa to the intestinal targets. A particularly preferred embodiment composition contains a mineral excipient for the selected Dapa in order to help homogeneous distribution of the composition to receptors.

BACKGROUND

Lower Gastrointestinal Tract Dysfunction.

The lower gastrointestinal tract [LGIT] is the section of the digestive tract from the pylorus to the anus. The walls of the LGIT are organized into four main layers: mucosa, submucosa, muscularis externa, and serosa. The mucosa consists of an epithelium with basement membrane, loose connective tissue, blood vessels, nerve endings, and lymph tissues (together called the lamina propria). The submucosa further supports the mucosa and also contains loose connective tissue, glands, blood vessels, nerve endings, and bundles of nerves called Meissner's plexus. The muscularis externa consists of two bands of smooth muscle cells, an internal layer of circular smooth muscle and external layer of longitudinal fibers. Interspersed between the muscle fibers is the plexus of Auerbach. The outermost layer of the digestive tube, the serosa, is composed of a membrane of squamous epithelium. The enteric mucosa, unlike the skin, does not have a keratin layer, and is thereby "non-keratinizing tissue".

The gut has a simplified "brain". The nerve network in the mucosa, submucosa, and myenteric plexuses has about 100 million neurons (the enteric nervous system). The submucosal Meissner's plexus regulates secretion by intestinal glands. The myenteric Auerbach plexus controls the rhythmic contraction of circular and longitudinal muscles [peristalsis]. Visceral nerve afferents are located throughout the mucosa, submucosa and the Meissner's plexus and the neuronal cell bodies are either in autonomic ganglia or in dorsal root ganglia. The sensory information from the gut is conveyed mainly via the vagus and splanchnic/pelvic nerves entering the spinal nervous system. Visceral sensations of pain and discomfort are also transmitted via sympathetic afferents into the spinal cord.

When the gut does not work properly, key elements of dysfunction usually originate from the enteric mucosa and, within it, the intrinsic nervous system. The epithelia of the LGIT have high metabolic activity and a turnover rate of about 5 days; that is, within 5 days, the entire lining is shed and renewed. This is a turnover of about ¼ pounds of cells per day. Many LGIT disorders are characterized by depletion of or damage to mucosa resulting from exposure to toxins, inflammation, autoimmune diseases, infections, etc. Typical symptoms are diarrhea and abdominal pain, and in the case of ulcerative colitis frequent passage of fresh blood through the anus [hematochezia].

A functional disorder of the LGIT is the irritable bowel syndrome [IBS]. Two organic diseases are ulcerative colitis and Crohn's disease, referred to as inflammatory bowel disease [IBD]. Other LGIT disorders are diverticulitis, celiac disease, lactose intolerance, chronic pancreatitis and regional ileitis. The clinical signs and symptoms of LGIT disorders include abdominal pain, a sense of distension or bloat, muscle spasms, decreased or increased frequency of bowel movements, intra-luminal bleeding, and flatulence. The pathophysiology is due to the disruption of intestinal (enteric) mucosal function and local inflammation. Current treatment for IBD includes anti-inflammatory drugs such as glucocorticosteroids, 5-aminosalicyclic acid (5-ASA, mesazaline), anti-spasmodic agents, anti-α-TNF drugs, and anti-diarrheal drugs. Surgery to remove the affected tissues [colectomy] is also used when the IBD is advanced as in ulcerative colitis.

In IBS aromatic oils can relax smooth muscle and relieve pain caused by cramps and gas. Peppermint oil is the most common agent in this class. Enteric-coated capsules containing peppermint oil have beneficial effects in IBS (Capello et al., Digestive and Liver Disease Peppermint oil (Mintoil®) in the treatment of irritable bowel syndrome: a prospective double blind placebo controlled randomized trial. 39: 530-536, 2007). Peppermint oil is 30 to 55% menthol and it is thought that menthol is the active ingredient in peppermint oil. Colpermin®, enteric coated capsules of peppermint oil, is approved for sale in Europe and in the United Kingdom, but not in the United States. Some of the constituents of peppermint oil, for example, pulegone may be toxic to the liver. Peppermint oil also contain 15 to 30% of menthone, a mutagen in the *Salmonella* Ames test [Andersen, P. H., Jensen, N.J., 1984. Mutagenic investigation of peppermint oil in the *Salmonella*/mammalian-microsome test. Mutat. Res. 138, 17-20]. The menthol content of peppermint oil is thought to locally diminish smooth muscle contractility and to reduce afferent discharge of sensory nerve endings. The recommended dosage for Colpermin® is three capsules per day; side-effects include diarrhea.

The LGIT actions of menthol and icilin, both "non-selective" TRPM8 receptor agonists, have been studied ["non-selective" means actions on more than one receptor types]. TRPM8 nerve endings, detected by immunoreactivity, are present in the LGIT. Menthol relaxes smooth muscle preparations (e.g. guinea pig ileum, and human colon) by blocking calcium channels on smooth muscle, but the mechanism is not via TRPM8. Icilin, a potent TRPM8 agonist, produces a contractile response in mouse colon and jejunum [Penuelas et al. 2007. Contractile effect of TRPA1 receptor agonists in the isolated mouse intestine. Eur. J. Pharmacol. 576, 143-50]. Hosoya et al. [2014. TRPM8 has a key role in experimental colitis-induced visceral hyperalgesia in mice. Neurogastroenterol. Motil. 26, 1112-21] administered WS-12, a selective TRPM8 agonist, and elicited a "freezing reaction" in mice with colitis, indicating that WS-12 produced pain and hyperalgesia, which are undesirable effects in colitis. Ramachandran et al. [TRPM8 activation attenuates inflammatory responses in mouse models of colitis. Proc. Natl. Acad. Sci. U.S.A. 110, 7476-81, 2013] showed that icilin reduced inflammation in a mouse model of colitis, a result supported by DeJong et al. [TRPM8 on mucosal sensory nerves regulates colitogenic responses by innate immune cells via CGRP. Mucosal. Immunol. 8: 491-504, 2015] who observed that TRPM8 knockout mice have a greater sensitivity to colitis.

Agonists are drugs that activate biological systems. Antagonists are drugs that sit on a receptor, block its function, but do not have intrinsic action on the receptor. Ramachandran et al. and DeJong et al. make a case the use of a TRPM8 agonist in LGIT dysfunction. Penuelas et al. and Hosoya et al. make a case for use of a TRPM8 antagonist.

Watson et al. [Compounds with the Menthol Cooling Effect. J. Soc. Cosmet. Chem. 29: 185-200, 1978] and Rowsell and Spring [Phosphine oxides having a physiological cooling effect, U.S. Pat. No. 4,070,496, 1978] synthesized a number of cooling agents with the goal of finding applications in comestibles and toiletries. Some of the compounds made by Watson et al. are known to act as TRPM8 agonists [Behrendt, H.-J. et al. 2004. Characterization of the mouse cold-menthol receptor TRPM8 and vanilloid receptor type-1 VR1 using a fluorometric imaging plate reader (FLIPR) assay. Br. J. Pharmacol. 141: 737-45, 2004].

BRIEF SUMMARY OF THE INVENTION

The present discovery pertains to a particular set of 1-[Dialkyl-phosphinoyl]-alkane molecules [Dapa]. Dapa are shown here to be selective agonists at the TRPM8 receptor. A preferred embodiment 1-Di(sec-butyl)-phosphinoyl-pentane, referred to herein as "DAPA-2-5", surprisingly and unexpectedly, potently relaxed human colonic muscle contractions in vitro. The inhibition of contraction was blocked by 1-benzyloxy-tryptamine (5-BT), a TRPM8 antagonist. DAPA-2-5 also inhibited the depolarization response of the isolated vagal nerve to capsaicin, a noxious agent, and showed an anti-inflammatory effect against heat-induced edema. Dapa and related species can be formulated for homogeneous delivery to the enteric mucosa. Consequently, Dapa with TRPM8 agonist activity, are useful, for example, in the treatment of LGIT dysfunction (e.g., diseases) as an antispasmodic agent and as an anti-inflammatory agent. Pharmaceutical compositions comprising Dapa designed for delivery to the intestinal lumen are proposed, such as in an enteric-coated tablet or capsule, or in a rectal suppository or enema, especially in formulations with mineral excipients such as magnesium aluminium silicates, are proposed for use in LGIT therapy.

Another aspect of the present discovery pertains to use of Dapa in the manufacture of a medicament for LGIT treatment (e.g. selective treatment of diseases), as described herein. Another aspect of the present discovery pertains to a method of treatment (e.g., selective treatment) of certain disorders (e.g., diseases), as described herein, comprising administering to a patient in need of treatment a therapeutically effective amount of Dapa, preferably in the form of a pharmaceutical composition. Another aspect of the present discovery pertains to a composition for formulations for topical delivery to the LGIT comprising a mixture with an inorganic mineral excipient, and in a suitable state of an enteric coated tablet or capsule. As will be appreciated by one of skill in the art, features and preferred embodiments of one aspect of the discovery will also pertain to other aspects of the discovery.

BRIEF DESCRIPTION OF THE SEVERAL VIEWS OF THE DRAWINGS

FIG. 5. are graphs showing the pharmacological activities of 1-[Dialkyl-phosphinoyl]-alkanes (Dapa). (A) Relative potencies of Dapa to menthol in TRPM8 assay. The number on the abscissa represent the n-alkyl side-chain of 4-5-6-7-8-9-10 carbons, corresponding to a butyl, pentyl, hexyl, heptyl, octyl, nonyl and decyl group, respectively. (B,C,D) Shaking frequency of anesthetized rats counted for 15 min, 40 min, and 1 h after intravenous 2 mg/kg, perioral 20 mg/kg, or topical 20 µL application of Dapa. From this pattern of response, DIPA-1-9 (the nonyl analog) is selected as the first choice to be a candidate for lower gastrointestinal tract dysfunction. The rank order of preferred embodiments is DAPA1-9>DAPA-1-8≥DAPA-2-8=DAPA-2-5>DAPA-2-7>DAPA-2-6. The rationale for the rank order is based on drug potency, duration of action, and drug delivery considerations for the LGIT luminal surfaces.

DETAILED DESCRIPTION OF INVENTION

A set of 1-[Dialkyl-phosphinoyl]-alkane molecules [abbreviated as Dapa] are proposed for the treatment of lower gastrointestinal tract [LGIT] disorders. Specific Dapa are coded as "DAPA-x" or "DIPA-x", where "x" is a numerical identifier. Dapa is a generic term, and Dipa refers only to diisopropyl analogs. A preferred embodiment, DAPA-2-5, inhibits afferent transmission of isolated mouse vagus in response to capsaicin, a noxious agent. DAPA-2-5 exhibits anti-inflammatory activity in a model of heat-induced edema. DAPA-2-5 is an antispasmodic agent when topically applied to isolated human colon muscle, an effect blocked by a TRPM8 antagonist. DAPA-2-5 is a first example of a water-soluble TRPM8 agonist that has this mode of action. Other preferred embodiments are DIPA1-8, DIPA-1-9, and DAPA-2-8. The preferred Dapa have a mechanism of drug action that may benefit LGIT disorders. In this section and in the "Study" examples, information is presented on: a) the chemistry of Dapa, b) the potency of Dapa on TRPM8, c) the selectivity of Dapa on TRPM8 receptors, d) the direct "antinociceptive" actions of Dapa on the isolated vagus nerve, e) the direct effects of Dapa on the human colon muscle strip, f) the anti-inflammatory actions of Dapa on heat-induced edema, g) laboratory studies in animals leading to the selection of the best Dapa ingredient, and h) discussion of Dapa formulationS for optimal delivery to the colon mucosa, including use of a mineral excipient.

Chemistry.

In one embodiment of the present invention, a composition is provided that comprises a 1-[Dialkyl-phosphinoyl]-alkane compound [Dapa] of Formula 1:

Formula 1.

wherein each of $R_1$, $R_2$, is either isopropyl or sec-butyl and $R_3$ is a linear alkyl group of 5 to 9 carbons, and total number of carbons is 13 to 16; and, in a formulation appropriate for delivery to the enteric mucosa.

The TRPM8 potencies of Formula 1 were determined in cells transfected with plasmids for TRPM8. The selected Dapa preferably are formulated in an enteric coated tablet or capsule or as a rectal suppository with mineral excipients. Thus, the composition is usefully delivered in a therapeutically effective amount to the intestinal lumen. The Dapa of Formula 1 is preferably represented by 1-[Di-sec-butyl-phosphinoyl]-pentane [DAPA-2-5], 1-[Di-sec-butyl-phosphinoyl]-octane [DAPA-2-8], 1-[Diisopropyl-phosphinoyl]-octane [DIPA-1-8], or 1-[Diisopropyl-phosphinoyl]-nonane [DIPA-1-9]. The rationale for selecting a particular Dapa for LGIT dysfunction is described in "Study 7".

Terminology and Abbreviations

Dapa and Dipa are the abbreviations for 1-[Dialkyl-phosphinoyl]-alkane and 1-[Diisopropyl-phosphinoyl]-alkane molecules, respectively. Dipa is a subset of Dapa. Other synonyms for this chemical group include: trialkyl-phosphine oxides, 1-dialkylphosphinoylalkanes, or 1-dialkylphophorylalkanes. The phosphorus is pentavalent in Dapa. The third alkyl group, $R_3$, in Formula 1 may be numbered as 4, 5, 6, 7, 8, and 9, corresponding to the butyl, pentyl, hexyl, heptyl, octyl, and nonyl, side chain, respectively. These alkanes are linear or "normal [n]" in configuration, with the phosphinoyl group attached to the primary, or "1-" position, of the carbon chain. Individual compounds are labelled as DAPA-x or DIPA-x where x is a numerical identifier. For the diisopropyl series, the "x" is 1-#, where # is the number of carbons in $R_3$. For the di-sec-butyl series, the "x" is 2-#. The syntheses of DIPA-5 to 7 and DIPA-9 were not previously reported but Siddall et al. [Simplified preparation of some trisubstituted phosphine oxides. J. Chemical Engineering Data 10: 303-305, 1965] reported the synthesis of DIPA 1-8 in 1965. There are no reports on biological activities of the DIPA synthesized here prior to this discovery. The DAPA-2-# series were made by Rowsell et al. Rowsell et al. are silent on the use of their Dapa compounds for LGIT disorders. The LGIT does not transmit any signals to the brain that are consciously recognized as cooling or cold. Thus, the action of TRPM8 agonists in the LGIT represents a new area of scientific discovery.

Lower Gastrointestinal Tract [LGIT] Dysfunction.

In the context of this application, "LGIT dysfunction" is meant to describe disorders such as irritable bowel syndrome, inflammatory bowel diseases, enteritis, colitis and proctitis; and specific disorders such as ulcerative colitis, Crohn's disease, diverticulitis, celiac disease, lactose intolerance, chronic pancreatitis, colon cancer, and regional ileitis. In the context of the instant application, LGIT dysfunction is also meant to include any one or more clinical sign and/or symptoms of the above-mentioned disorders. By "clinical sign" is meant an observed biological, physiological, biochemical, or pathophysiological feature of the disorder that is manifested by the patient and/or is an aid in its diagnosis. By "symptom" is meant a particular feature or features of a disorder that is "felt" or otherwise experienced by a subject having the disorder. For example, symptoms of uncontrolled smooth muscle contractions are cramping and abdominal discomfort, and seen in diabetic enteric neuropathy and in Crohn's disease. LGIT dysfunction is a significant economic burden on society [see, for example: Odes, S., 2008. How expensive is inflammatory bowel disease? A critical analysis. World J. Gastroenterol. 14, 6641-6647].

Irritable bowel syndrome (IBS, also known as Spastic Colon) is a disorder of the lower gastrointestinal tract (LGIT). Unlike inflammatory bowel disease (IBD), IBS patients do not manifest specific anatomic lesion in the gut mucosa. Some of the signs and symptoms of IBS/IBD are similar and include: cramping pain in the lower abdomen, bloating and distension, flatulence, tenesmus, diarrhea or constipation, immediate need to move the bowels after awakening or during or after meals, and feeling of incomplete emptying after bowel movements. Approximately, 10 and 20% of the population has had IBS at some time. The syndrome may appear in young adults but tends to begin in the second and third decades of life, causing bouts that recur at irregular periods. The cause of IBS is unknown. Examination of the rectal and colon surface does not reveal any irregular mucosal or vascular pattern; hence the term "functional" is applied to this order and not "organic".

In IBS/IBD, the circular and longitudinal muscles of the small and large intestines become hypo- or hyper-reactive to luminal constituents and the enteric control of contraction and relaxation is dysregulated. Intraluminal pressure studies show that constipation can occur in spite of increased frequency and amplitude of colon muscle contractions and, conversely, diarrhea can be occur with diminished motor function. Hyperactivity of the autonomic function may increase mucus production in the absence of epithelial injury. Hypersensitivity to normal intraluminal distention is present, together with pain perception in the presence of normal quantity and quality of intestinal gas.

No specific therapy is available for IBS. A physician's understanding and guidance is considered important for treatment. The physician is expected to reassure the patient that no organic disease is present. Anticholinergic drugs (muscarinic-blocking agents), such as atropine, opiate receptor agonists, such as loperamide, and antidepressants, such as imipramine, are prescribed to help the patient cope with diarrhea, abdominal pain and bloating. Peppermint oil in capsules is also used.

IBD is a much more severe disease with organic manifestations of injury and inflammation in the LGIT that can be visualized by endoscopy and histology, especially in the colon. About 1.2 million commercially insured individuals suffer from IBD in the USA [Kappelman et al. Recent trends in the prevalence of Crohn's disease and ulcerative colitis in a commercially insured US population, Dig. Dis. Sci. 58, 519-25 (2013)]. 5-Aminosalicylic acid [5-ASA] is the first drug of choice of IBD, but the disease is chronic and recurrent, and at least 20% of IBD patients may eventually require surgery [colectomy].

In both IBS and IBD, a topical Dapa antispasmodic agent delivered to the intestinal colonic/rectal surfaces with fast onset of action, will have therapeutic value. If a Dapa TRPM8 agonist also exerts anti-inflammatory action, this is even better. Animal models of IBD are proposed for further evaluation of Dapa anti-inflammatory effects in Study 6.

Formulation and Delivery of Dapa Compounds to Targets.

To be effective for LGIT dysfunction, Dapa are preferably taken orally, in a form to avoid systemic absorption and designed for topical release onto the enteric mucosa. If the affected area is primarily in the anorectal area, a suppository can also be considered. Systemic absorption should be avoided because if Dapa enters the circulation in sufficient amount it will stimulate sensory receptors in the body and cause shivering and cold. The GI tract is about 30 feet long, and the colon is 5 feet long at its distal end. Oral formulations are preferred but must traverse the stomach and jejunum, avoid enzymatic degradation, be subjected to variable pH, and encounter the microbiome before reaching target. The colon diameter is about 2 to 3 inches, with variable fluid volume and content (e.g dietary residues, intestinal secretions, mucus, and feces), and a transit time of 6 to 70 hr. The Dapa, once released in the LGIT, should have a uniform spreading capacity and retention time.

Colon-specific drug delivery strategies are well-known to the art and have been developed primarily for 5-ASA. For 5-ASA, these strategies include prodrugs, pH-dependent systems, time-dependence systems, and microflora-activated systems [Yang et al. Colon-specific drug delivery: New approaches and in vitro/in vivo evaluation, Int. J. Pharm. 235, 1-15 (2002).] Oral 5-ASA preparations are ~90% of the products sold, and intrarectal products are ~10%. Rectal products, mainly suppositories but also enemas, are considered more efficacious for drug delivery and therapy, but less accepted by the patient [Harris et al. Review article: delivery and efficacy of topical 5-aminosalicylic acid (mesalazine) therapy in the treatment of ulcerative colitis, Aliment. Pharmacol. Ther. 33, 996-1009 (2011)]. A consensus document also recommends the rectal route of administration of 5-ASA in preference to oral intake [Bressler et al. Clinical practice guidelines for the medical management of nonhospitalized ulcerative colitis: the toronto consensus, Gastroenterology 148, 1035-1058 (2015)].

Dapa are water soluble at therapeutically effective concentrations of 10 to 100 µg/mL and have molecular mass in the range of 232 to 274 Daltons. For oral formulations of Dapa, designed for "triggered" release of Dapa into the terminal ileum and colon, the likely coating/container are likely to be pH-dependent or time-dependent systems. These formulations are known to the art and have a polymer barrier to protect the tablet/capsule from dissolution in the esophagus, stomach and upper small intestine. The "protected" tablet or capsule will reach the LGIT mucosa and release the active ingredient [see examples described by Sandborn. Oral 5-ASA therapy in ulcerative colitis: what are the implications of the new formulations?, J. Clin. Gastroenterol. 42, 338-44 (2008)].

In one preferred embodiment, an effective amount of Dapa in an enteric coating is administered via oral ingestion of a tablet/capsule. A preferred unit dose is wherein Dapa is present in at about 5 to 200 mg per tablet/capsule. The enteric coatings are selected so as to remain intact in the upper GI tract pH, and to dissolve and release the contents of the dosage form in the environment of the LGIT. A common polymer for enteric coating is cellulose acetate phthalate (CAP). Another useful polymer is polyvinyl acetate phthalate (PVAP), which is less permeable to moisture and gastric fluids, and more stable to hydrolysis. An alternative polymer is hydroxypropyl methylcellulose phthalate. Polymers based on methacrylic acid, e.g., methacrylic acid ester copolymers with acidic ionizable groups, may also be considered. Dosage forms coated with methacrylic acid polymers dissolve in the ileum at about pH 6.8, and in the terminal ileum and caecum at about pH 7.2. In general, coating thicknesses of about 25 to 200 microns, and especially 75 to 150 microns, are preferred using about 3 to 25 mg, preferably 8 to 15 mg of acidic coating material per square centimeter of tablet or capsule surface. The precise coating thickness will also depend on compatibility with the mixture of Dapa and excipients Dapa, as a pure chemical, is a colorless or pale yellow liquid that is miscible with organic solvents (e.g. ethanol, 1,2-propanediol), liquid lipids (e.g. C8/10 glycerides or triglycerides or esters), and vegetable oils. These carriers may be used as excipients in a capsule or suppository. Dapa is also partially soluble in water at about 1% wt/vol. A liquid formulation in the capsule or suppository may not, however, be optimally delivered for the colon mucosa because of dispersion, penetration of drug past mucus and cell barriers, and retention time.

For oral or rectal administration, a strategy to homogeneously disperse the Dapa in an excipient is essential. In the preferred embodiment, Dapa is adsorbed onto a mineral excipient with a small defined particle size. A mineral excipient may be retained longer in the enteric mucosa and be a depot of slow drug release in close proximity to the mucosal targets. This new method of formulating Dapa in a mineral excipient is described in Study 8.

Methods for rectal administration include suppositories, enemas, and foams. The methods for making a rectal suppository, with suppository bases such as cocoa butter and other fatty acids, water-soluble or dispersible suppository bases such as polyethylene glycols, hydrogels and glycerinated gelatin are described in Remington's The Science and Practice of Pharmacy, 21$^{st}$ Edition. 2006. pg. 883-886. The Dapa can be adsorbed onto a mineral excipient and then dispersed, for example, into a polyethylene glycol matrix, and filled into a suppository.

It is well understood in the art that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

TRPM8 Mechanisms of Action on Gut.

"Cooling" is the psychical experience to heat abstraction from the body's surfaces. The subject may say it's cool, chilly, cold or icy cold. and the sites these sensations are identified as originating from the skin, orbit, nose, mouth, throat, upper esophagus, airways, and anogenital surfaces.

The detection of heat abstraction at these sites is principally via TRPM8, a neuronal protein linked to nerve membranes. In response to a decrement in temperature, TRPM8 creates "generator potentials" in the neuron, and when a critical threshold is reached there is an action potential [AP]. The AP is transmitted via a sensory nerve to the central nervous system and the location and the intensity of heat abstraction is perceived. The gut lining does not transmit signals that are interpreted by the brain as cooling or cold: that is, we never feel or say that our intestines feel cool or cold. The LGIT is maintained at constant body temperature by blood flow; hence a temperature sensing system is not required. But TRPM8-labeled neuronal fibers are present throughout the intestinal mucosa, especially in the Meissner's plexus, and to some extent in the Auerbach's plexus. Thus, TRPM8 pharmacology in the LGIT is a new area for scientific discovery. For example, TRPM8 may be part of the immune system in the LGIT that surveys and guards the epithelial cells from foreign substances in the gut. Also, TRPM8 may modulate peristalsis, detection of distension, mechanical activity, and pain.

Chemical agents can facilitate the activation of TRPM8 and increase TRPM8-linked AP, and influence local release of neurotransmitters. The binding site on TRPM8 for agonists may vary [i.e. which site on the six transmembrane loops of TRPM8 is affected]. The goal in TRPM8 therapy in LGIT dysfunction is to deliver a therapeutic TRPM8 agonist to a LGIT target. Understanding the matrix of the delivery site is important for selecting the correct TRPM8 drug because of LGIT geometry, motility, and contents. The selection of the drug candidate [active pharmacological ingredient or API] and its formulation is based on TRPM8 potency, molecular size, and lipophilic/hydrophilic characteristics that influence penetration/access to target, spreading capacity, activation pattern at receptor, and residence time. The API candidate must be selective for TRPM8 potency and not, for example, be active at TRPV1 or TRPA1, to produce the desired pharmacological effect, e.g. spasmolytic or anti-inflammatory, and be relatively free of eliciting sensory discomfort, e.g. chills or GI discomfort.

Peppermint oil, even though it is used in IBS, cannot be studied as an API under the standard conditions of modern pharmacology receptor concepts because it is a complex herbal mixture [Nair, B., 2001. Final report on the safety assessment of *Mentha Piperita* (Peppermint) Oil, *Mentha Piperita* (Peppermint) Leaf Extract, *Mentha Piperita* (Peppermint) Leaf, and *Mentha Piperita* (Peppermint) Leaf Water. Int. J. Toxicol. 20 Suppl 3, 61-73].

Menthol and icilin, are both non-selective ["non-selective" means actions on more than one receptor type] agonists at TRPM8 receptors (see references in Wei. Sensory/cooling agents for skin discomfort. Journal Skin Barrier Res 14: 5-12, 2012). These compounds are relatively water-insoluble. Menthol relaxes smooth muscle preparations (e.g. guinea pig ileum, and human colon) by blocking calcium ion channels on smooth muscle. Its effect on human colon muscle is not blocked by a selective TRPM8 antagonist such as 5-benzyyloxy-tryptamine (5-BT) DeFalco et al. 5-benzyloxytryptamine as an antagonist of TRPM8, Bioorg. Med. Chem. Lett. 20, 7076-9 (2010).

Icilin, a "superpotent" TRPM8 agonist [200× menthol], produces a contractile response in mouse colon and jejunum and has a mild effect on the activity of mechanosensory neurons in the gut. [Penuelas et al.; Harrington et al. 2011. A novel role for TRPM8 in visceral afferent function. Pain 152, 1459-68]. Hosoya et al. using a TRPM8 antibody, showed that TRPM8 immunoreactivity was present throughout the colon. Hosoya et al. administered WS-12, a potent and selective TRPM8 agonist, to mice with colitis and elicited a "freezing reaction". This reaction is viewed as a pain signal and the hyperalgesia observed is considered an undesirable effect in colitis. More recently, Ramachandran et al showed that icilin reduces inflammation in a mouse model of colitis. Ramachandran et al. postulated an anti-inflammatory role for icilin in colitis, a hypothesis that is supported by DeJong et al. [2015. TRPM8 on mucosal sensory nerves regulates colitogenic responses by innate immune cells via CGRP. Mucosal. Immunol. 8: 491-504]. De Jong et al. observed that TRPM8 knockout mice have a greater sensitivity to colitis. Both Ramachandran et al. and DeJong et al. proposed that TRPM8 regulation of CGRP [calcitionin-gene related peptide] release from sensory neurons in the gut nerves may modulate inflammation events in colitis, although Ramachandran et al. view CGRP as being harmful and DeJong et al. view CGRP as being helpful in controlling the inflammation of colitis.

The observations of Hosoya et al. and Penuelas et al. make a case for use of a TRPM8 antagonist to alleviate the spasms and discomforts of colitis. The studies of Ramachandran et al. and de Jong et al. make a case for the use of a TRPM8 agonist as an anti-inflammatory agent in LGIT dysfunction. Wei has synthesized a number of Dapa, similar to those described by Rowsell and Spring. ["Phosphine oxides having a physiological cooling effect", U.S. Pat. No. 4,070,496, 1978]. Rowsell and Spring did not study Dapa for effects on the lower gut. Dapa compounds inhibit neurotransmission in the isolated vagus nerve, an "anti-afferent" action that is desirable for reducing visceral pain detection. DAPA-2-5 is an anti-inflammatory agent on heat edema. Surprisingly and unexpectedly, I find here that Dapa relaxed human colonic smooth muscle, an effect blocked by the TRPM8 antagonist (5-BT). The median effective concentration for inhibition of contraction was 8 μg/mL, a concentration that can be attained with topical formulations to the LGIT. Together these data show that TRPM8 agonists have value in the treatment of LGIT dysfunction. A strategy was devised by Wei for selecting and formulating delivery of a preferred Dapa to the enteric mucosa. It was discovered that an ideal excipient for spreading Dapa to the intestinal walls was by formulation of Dapa in a mineral excipient. These findings are further described in the "Study" section.

Study 1

Chemical Synthesis and Receptor Assays The compounds tested here are trialkyl derivatives of phosphoric acid (Dapa), in which two of the alkyls are either isopropyl or sec-butyl, and the third alkyl is $C_4$ to $C_{10}$ (Table 1). The Dapa in the Table 1 were custom synthesized using this general method: 100 mL (23.7 g, ~200 mmol) of isopropylmagnesium chloride or sec-butylmagnesium chloride were obtained from Acros, as a 25% solution in tetrahydrofuran (THF) and placed under nitrogen in a 500 mL flask (with a stir bar). Diethylphosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 min, followed by a drop-wise addition of the appropriate n-$C_4$ to $C_{10}$ iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVapBuchi, bath temperature 40° C.). The light brown oil was distilled under high vacuum (0.5 mm Hg). The final products, mass verified by mass spectrometry, were liquids that were colorless or slightly pale yellow and have boiling points in the range of 120 to 130° C. Several samples of DAPA-2-5, DIPA-1-7, and DIPA-1-9 were analyzed by GC-MS (NCE Corporation, Pleasanton, Calif., USA, www.nceanalytical.com) on an Agilent GC/MS system 6890/5973 equipped with a Trace Gold TG-624 column, with helium as the carrier gas (flow rate: 1.6 mL/min) and the injector port set at 220° C. (split ratio 50:1, temperature program: 100 to 240° C.). The total ion chromatogram (TIC) showed the main components with a retention time of 13 to 14 min, and 18 to 19 min, and the detected peaks accounted for 98.7% and 97.2% of total area, for DIPA-1-9 and DIPA-1-7, respectively.

TABLE 1

Chemicals prepared and tested.

| Code | Chemical Name | Chemical Structure |
|---|---|---|
| DIPA-1-5 | 1-Diisopropyl-phosphinoyl-pentane |  |
| DIPA-1-6 | 1-Diisopropyl-phosphinoyl-hexane |  |
| DIPA-1-7 | 1-Diisopropyl-phosphinoyl-heptane |  |
| DIPA-1-8 | 1-Diisopropyl-phosphinoyl-octane |  |
| DIPA-1-9 | 1-Diisopropyl-phosphinoyl-octane |  |
| DAPA-2-4 | 1-Di(sec-butyl)phosphinoyl-butane |  |
| DAPA-2-5 | 1-Di(sec-butyl)phosphinoyl-pentane |  |
| DAPA-2-6 | 1-Di(sec-butyl)phosphinoyl-hexane |  |

TABLE 1-continued

Chemicals prepared and tested.

| Code | Chemical Name | Chemical Structure |
|---|---|---|
| DAPA-2-7 | 1-Di(sec-butyl) phosphinoyl-heptane | |
| DAPA-2-8 | 1-Di(sec-butyl) phosphinoyl-octane | |
| DAPA-3-1 | 1-Di(iso-butyl) phosphinoyl-pentane | |
| DAPA-3-2 | 1-Di(sec-butyl) phosphinoyl-3-methyl-butane | |

Study 2.

TRPM8 Receptor Assays: Agonist Activities

Compounds were tested on (CHO) cells stably transfected with human TRPM8 cDNAs using a Fluo-8 calcium kit and a Fluorescence Imaging Plate Reader (FLIPRTETRA™) instrument. Assays were conducted by ChanTest Corporation, 14656 Neo Parkway, Cleveland, Ohio 44128, USA. Solutions were prepared by diluting stock solutions in a HEPES-buffered physiological saline (HBPS) solution. Test compound and control formulations were loaded in polypropylene or glass-lined 384-well plates, and placed into the FLIPR instrument (Molecular Devices Corporation, Union City, Calif., USA). Each was tested at 8 concentrations with n=4 replicates per determination. The positive control reference compound was I-menthol, a known TRPM8 agonist. For FLIPRTETRA™ assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of test compound, vehicle, or control solutions in HBPS were added to each well and read for 4 minutes. Concentration-response data were analysed via the FLIPR Control software that is supplied with the FLIPR System (MDS-AT) and fitted to a Hill equation. The 12 compounds tested showed full efficacy on the TRPM8 receptor, i.e., at higher tested concentrations there was ~100% stimulation of calcium entry, and the data fitted a sigmoidal dose-response curve.

TABLE 2

EC$_{50}$ and relative potency of compounds on TRPM8..

| Code | EC$_{50}$ μM | 95% Confidence Interval | Relative Potency |
|---|---|---|---|
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| DAPA-2-4 | 14.5 | 7 to 29 | 0.3 |
| DAPA-2-5 | 1.7 | 1.0 to 2.9 | 2.2 |
| DAPA-2-6 | 0.8 | 0.5 to 1.3 | 4.7 |
| DAPA-2-7 | 1.1 | 0.6 to 2.3 | 3.4 |
| DAPA-2-8 | 1.3 | 0.7 to 2.3 | 2.9 |
| DAPA-3-1 | 24 | 8 to 76 | 0.2 |
| DAPA-3-2 | 4.2 | 1.6 to 10.8 | 0.9 |

The EC$_{50}$ of the more potent compounds (DIPA-1-7, DIPA-1-8, DIPA-1-9, DAPA-2-5, 2-6, DAPA-2-7, DAPA-2-8) fell within a narrow range with overlapping 95% Confidence Intervals. [Table 2] The potency of DIPA-1-7 and DIPA-1-8 are similar and significantly greater than the potencies of DIPA-1-5 and DIPA-1-6. By contrast the structural modifications of comparative compounds 3-1 and 3-2 resulted in a significant loss of bioactivity. DIPA-1-10 was synthesized at a later time and tested by David Andersson of King's College, London, U.K. It was found to be 2.4× less active than DIPA-1-9 [or 1.7× menthol on Table 3]. The data for DIPA-1-10 is not included in the Table 2 or Figure because it was obtained under different assay conditions.

Study 3
TRPA1, and TRPV1 Assays: Selective Receptor Activity

Receptor selectivity is a basic concept in pharmacology. If a molecule acts on multiple receptors then it is likely to have "off-target" effects, create uncertainty, and increase the risks of adverse effects. The TRP family of neuronal proteins are linked to sensory perception. TRPV1 and TRPA1 are nociceptive receptors: activation of these C-fiber linked receptors lead to irritation and pain. Thus, it is imperative to test preferred Dapa on TRPV1 and TRPA1, and show that these receptors are not activated. 2-5, 1-8, and 1-9 are "pure" TRPM8 agonists, 1-7 is also selective but there is a hint that 1-7 may affect the baseline response to TRPV1. Up to 50% of TRPM8 neurons also have TRPV1 present in the same neuron. Thus, the absence of TRPV1 activity in a Dapa is of critical importance.

Figure 1:
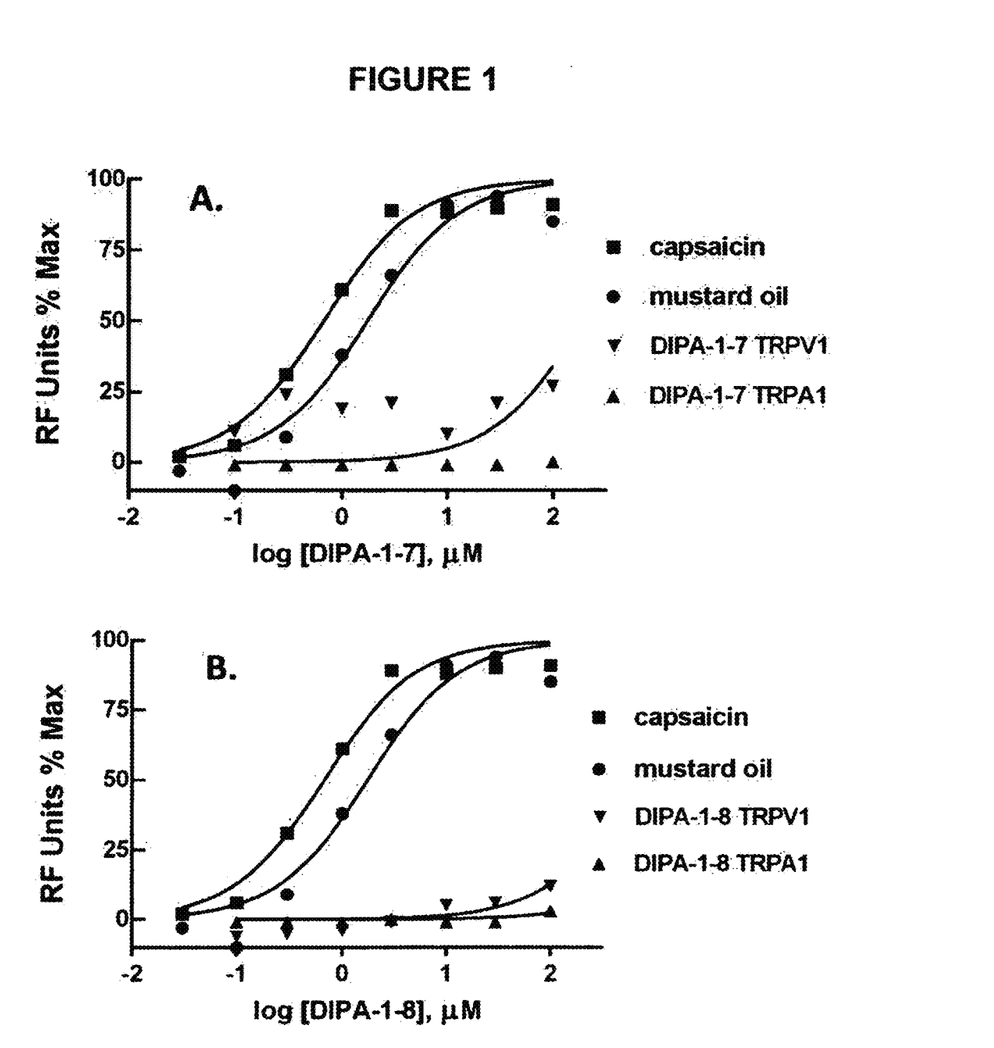
FIG. 1. is a graph showing the lack of agonist activity of DIPA-1-7 (A.) and DIPA-1-8 (B.) in cells transfected with TRPV1 or TRPA1 plasmids. The positive controls capsaicin and mustard oil for TRPV1 and TRPA1 are active, respectively, but DIPA-1-7 and DIPA-1-8, by comparison, are less active in TRPV1 or TRPA1 transfected cells. The ordinate is given in Relative Fluorescence Units % of maximum, which measures calcium entry into the transfected cells, and the abscissa is logarithm of the concentration of the test compound.

The selectivity of test compounds were examined on TRPV1 channels (human TRPV1 gene expressed in HEK293 cells) and TRPA1 channels (human TRPA1 gene expressed in CHO cells). The test cells were Chinese Hamster Ovary (CHO) cells or Human Embryonic Kidney (HEK) 293 cells transfected with human TRPV1 or TRPA1 cDNAs. The positive control reference compound was capsaicin (a known TRPV1 agonist) or mustard oil (a known TRPA1 agonist). As shown in FIG. 1, DIPA-1-7 and DIPA-1-8 did not exhibit significant agonist on antagonist activity on TRPV1 or TRPA1 channels at maximum tested concentrations of 100 µM. Similar results were also obtained for DAPA-2-5 and DIPA-1-9.

FIG. 1. are graphs showing the lack of agonist activity of DIPA-1-7 (A) and DIPA-1-8 (B) in cells transfected with TRPV1 or TRPA1 plasmids. The positive controls capsaicin and mustard oil for TRPV1 and TRPA1 are active, but DIPA-1-7 and DIPA-1-8 are not. The ordinate is given in Relative Fluorescence Units; % of maximum, which measure calcium entry into the transfected cells and the abscissa is the logarithm of the concentration of the test compound. DIPA-1-7 and DIPA-1-8 were also devoid of antagonist activity. A slight non-dose-dependent agonist action of DIPA-1-7 was observed on TRPV1.

DAPA-1-9 was tested on TRPV1 channels and TRPA1 channels expressed in KNRK cells (Kirsten murine sarcoma virus transformed kidney epithelial cells). KNRK cells were cultured as a monolayer and maintained in DMEM (Life Technologies), supplemented with 10% FBS (Life Technologies), 100 units/ml penicillin and 100 µg/ml streptomycin, in an incubator of 5% $CO_2$ at 37° C. After suspension, the cells were coated on cover slips for 12 hours, then transiently transfected with cDNA (pc3.1 DNA) for TRPV1 or TRPA1 with Lipofectamine 2000 (Invitrogen) for 24 hr, and loaded with Fura-2AM™ (Molecular Probes) for 40 min at 37° C. After washing and recovery, KNRK cells were imaged at 340 and 380 nm excitation to detect free calcium influx. An increase of 50% of the 340/380 ratio was considered as the response threshold which were measured under blinded conditions for plasmids. Compounds were applied to the bath and calcium response was acquired by an inverted Nikon fluorescence microscope with a CoolSnap HQ2 CCD camera (Photometrics, Tucson, Ariz.). Data were quantified offline with the Nikon-NIS program. DAPA-1-9 like DAPA-1-8 was devoid of agonist or antagonist activities against TRPV1 or TRPA1.

Study 4
Isolated Vagus Nerve Preparation: Direct Anti-Nociceptive Activity of Dapa The vagus nerve is an important autonomic sensory nerve of the gut. It is the largest sensory cranial nerve in the body. The colon is also innervated by the splanchnic and pelvic nerves. Technically, measurement of activity of single unit afferents from the gut is difficult, but nerve transmission of an isolated segment of the vagus is a good surrogate. An agent that inhibits neural transmission in the vagus in response to a noxious agent such as capsaicin predicts peripheral antinociceptive activity.

Figure 2:
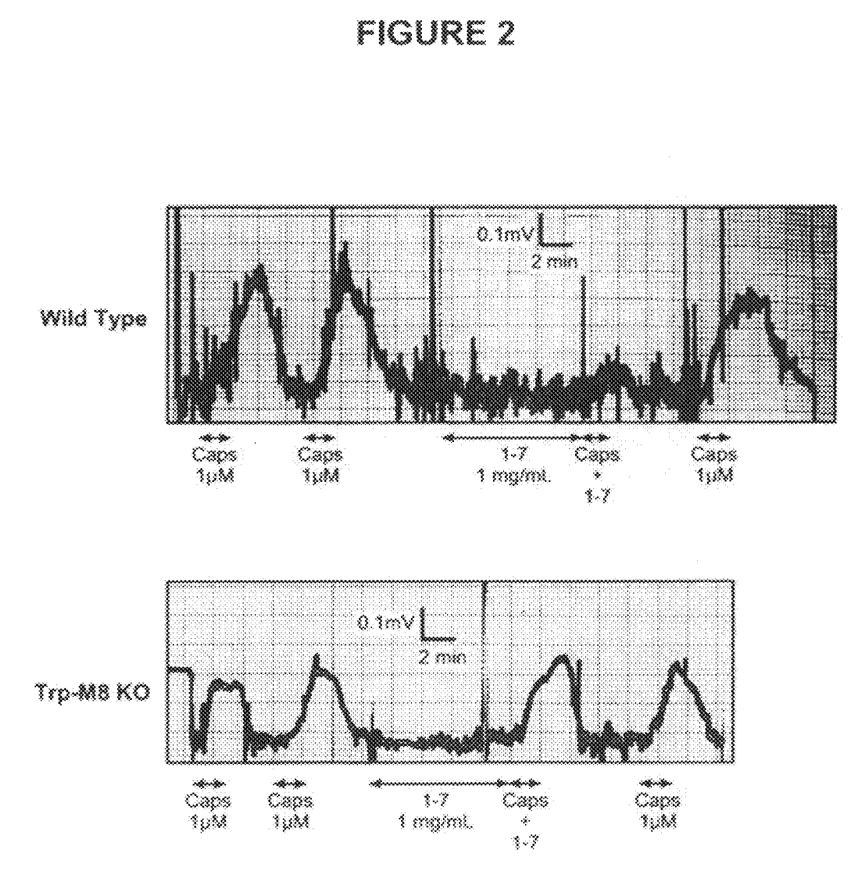
FIG. 2. is a graph showing the effect of DIPA-1-7 embodiment, 1 mg/mL, on capsaicin-induced depolarization of the isolated mouse vagus. In the first trace ("Wild Type"), DIPA-1-7 superfused on the nerve inhibits depolarization, and, in the second trace ("TRPM8 KO"), the inhibition of DIPA-1-7 is reduced in TRPM8 KO (knockout) vagus.

An isolated vagus nerve model was developed at Imperial College, London, U.K. [Birrell et al. TrpA1 agonists evoke coughing in guinea pig and human volunteers. Amer. J. respiratory and critical care medicine 180, 1042-7, 2009; Patel, H. J. et al. Inhibition of guinea-pig and human sensory nerve activity and the cough reflex in guinea-pigs by cannabinoid (CB2) receptor activation. Brit. J. Pharmacol. 140, 261-8, 2003]. In this in vitro assay, segments of the mouse vagus nerve are placed on a platform and the electrical activity is recorded after topical application of capsaicin. Capsaicin is a known irritant that elicits pain when it is applied to the skin and it will depolarize the isolated vagus. The ability of Dapa agonists DIPA-1-7 to inhibit this capsaicin-induced depolarization were measured as shown in FIG. 2. The similar effect of DAPA-2-5 in this test system was published in U.S. Ser. No. 14/55,042.

Briefly, segments of vagus nerve, caudal to the nodose ganglion, were removed from mice with fine forceps and segments placed in oxygenated Krebs solution and bubbled with 95% $O_2$/5% $CO_2$. The desheathed nerve trunk was mounted in a 'grease-gap' recording chamber and constantly superfused with Krebs solution with a flow rate of approximately 2 mL/min, and the electrical activity of the nerve monitored with electrodes. The temperature of the perfusate was kept constant at 37° C. by a water bath. Nerve depolarizations were induced by superfusion of the nerve with capsaicin (1 µM). After two reproducible depolarization responses to capsaicin, DIPA-1-7 was applied at 1 mg/mL for 10 minutes in the perfusate followed by capsaicin. The nerves were then washed with Krebs until the responses had returned to baseline and challenged again with capsaicin. The results and tracings obtained in normal and TRPM8 knockout mouse are shown in FIG. 2.

FIG. 2 shows chart traces that illustrate, in the first trace ("Wild Type"), the inhibition of capsaicin-induced depolarization of the isolated mouse vagus by DIPA-1-7, superfused at a concentration of 1 mg/mL, and, in the second trace ("TRPM8 KO"), the significant absence of inhibition in the isolated TRPM8 KO (knockout) mouse vagus by DIPA-1-7, superfused at a concentration of 1 mg/mL. The percent inhibition of capsaicin-induced depolarization of the isolated normal mouse vagus caused by DIPA-1-7 was about 75%; the percent inhibition of capsaicin-induced depolarization of the isolated TRPM8 knock-out mouse vagus caused by DIPA-1-7 was about 20%.

This experiment clearly demonstrates a direct pharmacological action of the DIPA-1-7 on the sensory nerve, which is a surprising and unexpected result. Furthermore, the diminished response in the TRPM8 KO mouse indicated that the receptor target was TRPM8. These results provide strong evidence that DIPA-1-7 can be used as an anti-nociceptive agent and the target receptor is TRPM8.

Capsaicin is a TRPV1 agonist and the search for an effective TRPV1 antagonist has been the super-intense quest of many pharmaceutical companies for the past ten+ years. Here, it is shown that DIPA-1-7 is an effective "physiological" antagonist of TRPV1 at low concentrations. DIPA-1-7, by itself, did not evoke depolarization, indicating that it is free of agonist activity at this "pain" receptor. The results illustrate the potential utility of DIPA-1-7 as an anti-nociceptive agent. A near identical set of data were obtained for DAPA-2-5 and shown in U.S. Ser. No. 14/544,042. The percent inhibition of capsaicin-induced depolarization of the isolated normal mouse vagus caused by DAPA-2-5 was 60%. DAPA2-5 did not inhibit the capsaicin-induced depolarization in the TRPM8 knock-out mouse.

Study 5

Dapa and Human Circular Gut Muscle

A key paper on menthol effects on the smooth muscle of the human distal colon is by Amato et al. [Effects of menthol on circular smooth muscle of human colon: Analysis of the mechanism of action. (2014) Eur J Pharmacol. 740: 295-301]. She concluded that: "Menthol exerts its inhibitory effects in a TRPM8-independent manner, by acting as an antagonist of the smooth muscle L-type $Ca^{2+}$ channels". This result confirmed earlier data on the guinea pig ileum muscle preparation, and is based on observations that menthol actions are blocked by nifedipine, a calcium channel antagonist, but not by 5-benzyloxy-tryptamine [5-BT], a TRPM8 antagonist. Amato's use of human colon tissue, the first time this has been done, removed any doubts about species differences in drug response to menthol, as previous data were only from guinea pigs, rats, and mice. Amato et al. also noted that WS-12, a TRPM8 agonist, was active in the muscle preparation and was blocked by 5-BT. Thus, a TRPM8 sensitive element is present in colon tissues.

Tsavaler et al. [Trp-p8, a novel prostate-specific gene, is up-regulated in prostate cancer and other malignancies and shares high homology with transient receptor potential calcium channel proteins. Cancer Research 61:3760-3769, 2001.] cloned a protein from the prostate gland and called it "trp-p8". Afterwards, it was discovered that this protein was also present in neurons and transduced sensations of heat abstraction. The name for "trp-p8" is now TRPM8. TRPM8 is abundantly expressed in the prostate and liver, but functions of TRPM8 in such tissues are not known. TRPM8 was called the coldl/menthol receptor [CMR1] (McKemy et al. 2002. Identification of a cold receptor reveals a general role for TRP channels in thermosensation. Nature 416, 52-8]. But this nomenclature is not correct for the LGIT, liver, or prostate, where there are no sensations of cold, and where, for the LGIT, menthol acts on a different target. The pharmacology of TRPM8 in the gut is a new and unexplored entity. Menthol/peppermint oil, the active agents on gut muscle, do not work via TRPM8. But how about Dapa?

In this present study, Dapa was examined by Amato in her test system. Surprisingly, Dapa exerted a potent inhibitory effect on spontaneous mechanical activity of human circular smooth muscles cells, and this effect was TRPM8-dependent. As shown in the FIG. 3, DAPA-2-5, prepared as a solution dissolved in distilled water, produced a dose-dependent reduction of the amplitude of human colon smooth muscle contractions when it was added to the organic bath. The DAPA-2-5 median inhibitory concentration ($IC_{50}$) was 34 μM, or 8 μg/mL. This effect was inhibited by pretreatment with 5-BT ($10^{-5}$ M), a selective TRPM8 antagonist. The result shows, for the first time, that human TRPM8 is responsive to Dapa in the colon, and that Dapa can be used to treat LGIT dysfunction.

The experimental procedures were approved by the Ethics Committee, University of Palermo, Italy. Human distal colon samples were obtained after informed consent from patients without LGIT disorders. The specimens were immediately placed in preoxygenated Krebs solution and stored overnight at 4° C. Circular muscular strips (4 mm wide by 10 mm long) were cut and suspended in a four-channel organ bath and connected to an isometric force transducer (FORT 25, Ugo Basile, Biological Research Apparatus, Comerio, Va., Italy). The organ bath contained 8 mL of oxygenated Krebs solution at 37° C. Mechanical activity was analyzed using the PowerLab/400 system (Ugo Basile). A tension of 1 g was applied, and strips allowed to equilibrate until spontaneous phasic contractions were recorded. Dapa compounds were added at step concentrations of 1 to 300 μM to the organ bath, with washing in between, and the contractions recorded after 4 min when the drug effect stabilizes. The TRPM8 antagonist, 5-BT ($10^{-5}$ M), was added at least 15 min before Dapa.

Figure 3:
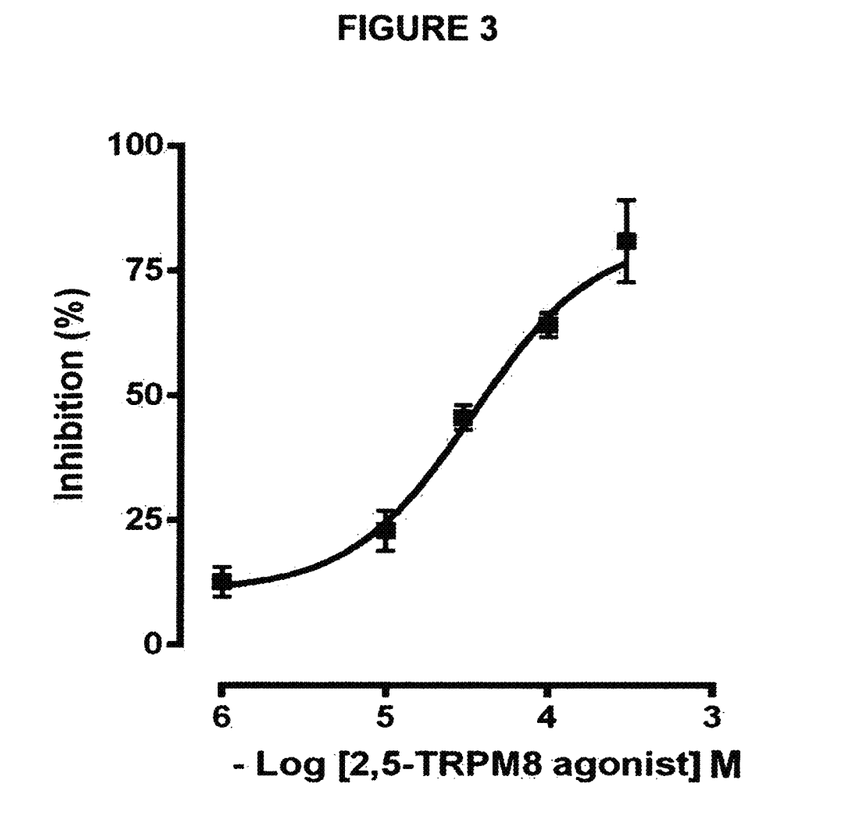
FIG. 3. Is a graph showing the dose-concentration relationship of DAPA-2-5 on spontaneous contractions of the human circular smooth muscle in vitro. The median inhibitory concentration (IC50) of DAPA-2-5 was 8 µg/mL.
Figure 4:
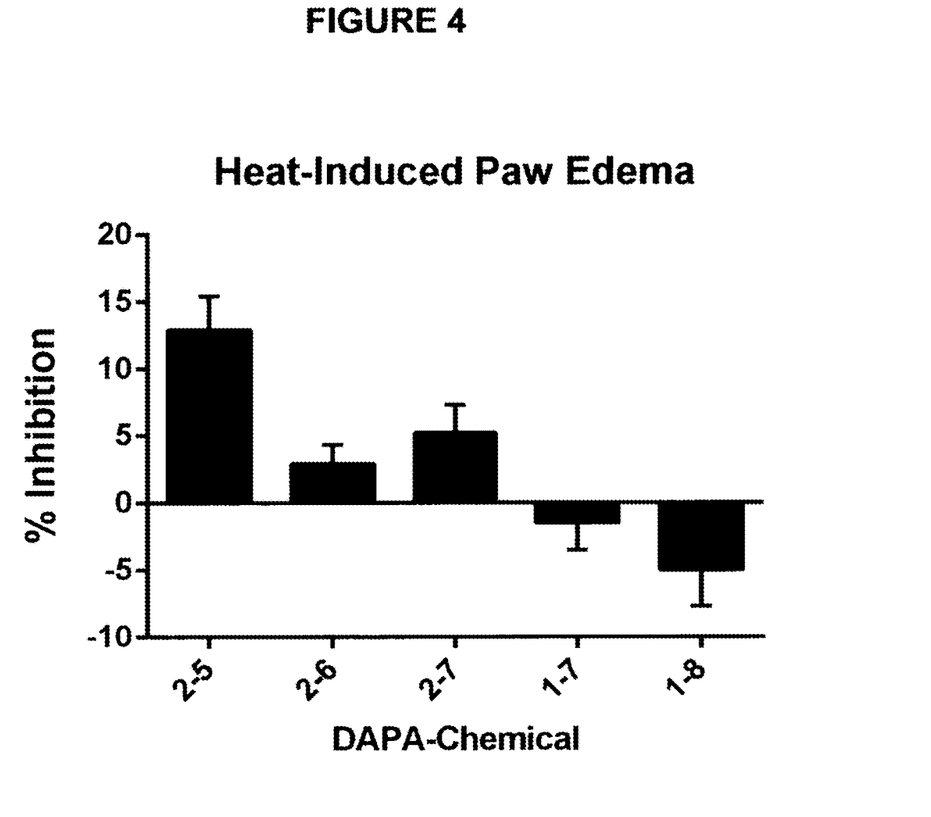
FIG. 4. Is a graph showing the relative activity of Dapa compounds for the inhibition of heat-induced edema in the anesthetized rat paw. DAPA-2-5 exposure significantly inhibited heat-induced edema relative to the contralateral paw by 12.9% (P<0.01). This effect shows that DAPA-2-5 had anti inflammatory properties.

FIG. 3. Is a graph showing the dose-concentration relationship of DAPA-2-5 on spontaneous contractions of the human circular smooth muscle in vitro. The median inhibitory concentration ($IC_{50}$) of DAPA-2-5 was 8 μg/mL.

Study 6

Anti-Inflammatory Activity on Heat-Induced Edema

Inflammation is defined as the reaction of vascularized living tissue to local injury [Cotran, R S. 1989. Inflammation and repair. In Robbins: Pathologic Basis of Disease, ed. S. L. Robbins, R. S. Cotran, V. Kumar, 2:39-86. Philadelphia: Saunders. $4^{th}$ ed.]. The characteristic signs of inflammation are redness, swelling, heat, and pain (and loss of function). The anti-inflammatory properties of the DAPA compounds were studied in a model of heat-induced vascular leakage [Wei et al. Method of inhibiting inflammatory response. U.S. Pat. No. 4,801,612; Wei et al., Anti-inflammatory peptide agonists. Annual Review Pharmacol Toxicol. 33:9-108, 1993]. When the paws of pentobarbital-anesthetized rats (200 to 300 g body weight) are immersed in 58° C. water for 1 min, the normal paw volume of about 1.8 mL was increased by ~88% within 30 min, the swelling being due to an increase in water content of the paw. The test was to see if the paw is exposed for 30 min before heat to selected DAPA compounds reduced the heat-induced increases in paw volume.

Test compounds were dissolved in 20% water-80% R-1, 2-propanediol at 20 mg/mL. The solutions were applied to the paw skin of pentobarbital-anesthetized rats (200 to 300 g body weight) at 0.3 mL per paw, using a syringe attached to a blunt 21 gauge needle covered at its tip with a piece of polyethylene 60 tubing. After distributing the solution over the paw, the paw was tightly enclosed in a plastic finger cut from a disposable glove. The contralateral paw [control] received only the vehicle. Thirty min after application, both paws were immersed in 58° C. water for 1 min. Thirty min after immersion, both paws were cut at ankle joint with scissors and weighed.

In preliminary studies, it was found that the paws of control animals (N=12) increased in weight from 1.77±0.02 g (mean±S.E.M.) to 3.33±0.07 g after heat exposure (58° C. water for 1 min), an increase in paw weights of 88±2%. As shown by the data in FIG. 2, DAPA-2-5 significantly inhibited this response, relative to the contralateral paw, by 12.9% (P<0.01). This degree of inhibition is significant for tissue protection as the injury stimulus is of supra-maximal intensity. The DAPA-2-5 effect was apparent to the untrained observer. These results were surprising because this anti-inflammatory property of DAPA-2-5 was not expected, and had not been previously reported in the scientific literature; furthermore, the inhibitory effects of DAPA-2-5 were not seen for the other DAPA compounds.

The mechanisms of heat-induced edema have been discussed elsewhere [Reed et al., Transcapillary exchange: role and importance of the interstitial fluid pressure and the extracellular matrix. Cardiovascular Res. 87: 211-217, 2010]. The denatured proteins of the heat-injured tissues unfurl and expose hydrophilic groups. The decreased interstitial fluid pressure of the extracellular matrix then imbibes water from the blood compartment into the skin. This results in rapid tissue edema. DAPA-2-5 inhibits this process but not the other tested DAPA compounds [see FIG. 2].

TABLE 3

Effects of test compounds on heat edema.

| Compound | Mol. Wt. | Inhibition of Heat Edema (±S.E.M.) |
| --- | --- | --- |
| DAPA-2-5 | 232 | 12.9 ± 2.5* |
| DAPA-2-6 | 246 | 2.9 ± 1.4 |
| DIPA-2-7 | 260 | 5.2 ± 2.1 |
| DIPA-1-7 | 232 | −1.5 ± 2.0 |
| DIPA-1-8 | 246 | −5.0 ± 2.7 |

*$P < 0.01$ vs contralateral paw

The inflammation of IBD is more complex and may have an autoimmune basis. In IBD, an antigen is recognized by immune cells, e.g. dendritic cells or cells of Langerhans, and an antibody reaction is generated in the lymphoid tissues. Subsequent antigen-antibody reactions release chemokines and cytokines that cause inflammation. The primary elements of an anti-inflammatory effect: namely, reduced permeability of blood vessels, less edema, and antinociception, predicted by the Dapa agent, DAPA-2-5, on heat-edema experiments will, however, benefit localized intestinal inflammation.

To further characterize Dapa, future studies can be done on animal models of intestinal inflammation. These are well-known to the art and consist of administering to rats or mice, 2,4,6-trinitrobenzene sulfonic acid (TNBS) or dextran sodium sulfate (DSS) [Wirtz et al. Chemically induced mouse models of intestinal inflammation. Nature Protocols 2: 541-547, 2007]. TNBS or DSS is given by the intrarectal route or in drinking water. Colitis can be induced in about 2 weeks after 5 days of dosing, or in the chronic version of the disease, in 2 months. Indications of colitis severity can be quantified by body weight loss, increased production of inflammatory cytokines such as TNF-α, IL-6 and IL-1β, and histology of intestinal mucosa. A Dapa such as DIPA-1-9 can, in experiments, be administered by gavage or subcutaneous injections or it can be administered in the drinking water with an adjunct. In Study 9 DAPA-2-5 was mixed with condensed milk [8.5%] at 0.5 mg/mL and liquid consumption was monitored. The averaged intake of DAPA-2-5 in the treated group [N=12 rats] was 41 mg/kg body weight/day for 40 days. Thus, one method of administration is to induce animals to drink large quantities of Dapa on a daily basis. Dapa can also be studied on epithelial cells, inflammatory cells, and neuronal cells; especially in relationship to calcium entry into cells and CGRP release, as CRGRP appears to be a controlling factor in immune response and local inflammation of the LGIT. These experiments will clarify the mechanisms of action of Dapa in LGIT dysfunction.

Study 7

Comparison of Dapa Activity after Perioral, Topical and Intravenous Delivery

Figure 5:
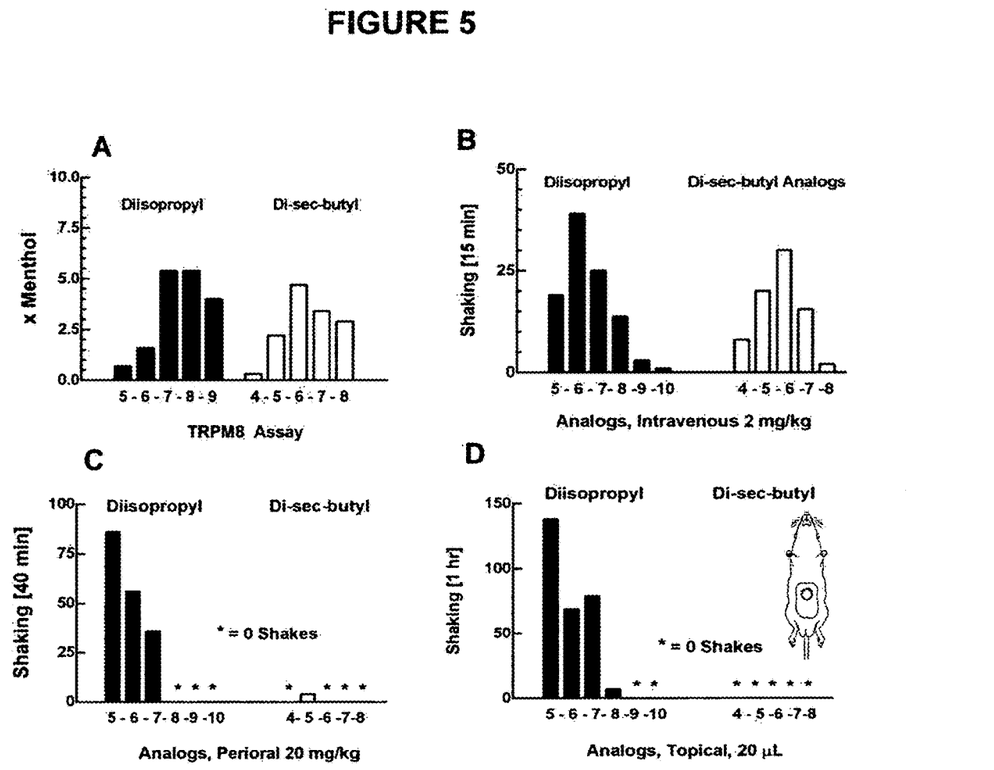

Dapa was administered to rats by the intravenous, perioral, and topical routes and shaking frequency was counted (FIG. 5 and Table 4). This study gives information on the ability of Dapa to cross membrane barriers and is important for the selection of the lead candidates for the treatment of LGIT dysfunction.

FIG. 5. are graphs showing the pharmacological activities of 1-[Dialkyl-phosphinoyl]-alkanes (Dapa). (A) Relative potencies of Dapa to menthol in TRPM8 assay. The number on the abscissa represent the n-alkyl side-chain of 4-5-6-7-8-9-10 carbons, corresponding to a butyl, pentyl, hexyl, heptyl, octyl, nonyl and decyl group, respectively. (B,C,D) Shaking frequency of anesthetized rats counted for 15 min, 40 min, and 1 h after intravenous 2 mg/kg, perioral 20 mg/kg, or topical 20 μL application of Dapa, respectively. From this pattern of response, DIPA-1-9 (the nonyl analog) is selected as an ideal candidate for LGIT dysfunction. Alternative preferred embodiments are DAPA-2-5, DAPA-2-8, and DIPA-1-8, with DAPA-2-6 and DAPA-2-7 being the final choices.

Fur-coated and feathered animals—when wet and cold—shake, like a wet dog (see, e.g., Dickerson et al., 2012; Ortega-Jimenez et al., 2012; Wei, 1981). These shakes are rapid alternating contractions of the supination and pronation muscles about the spinal axis, and can be readily observed and counted. "Wet-dog shaking" has survival value because shaking, by removing the water off the skin, reduces expenditure of evaporative energy to remove wetness. The sensation for initiating shaking is water trapped between hair follicles or feathers. Humans have little hair on skin and do not shake. The likely equivalent behavior to shaking in humans is shivering, a condition caused by generalized sensations of coolness/cold and wetness. Drug-induced shaking in animals has been reviewed (see, e.g., Wei, 1981). Under the right conditions, drug-induced shaking can be observed in the pentobarbital-anesthetized rat, enhanced by hypothermia and cold, and inhibited by elevating body temperature.

In experiments conducted here, test compounds were evaluated for "wet-dog shaking" as a model of cooling sensation. Using a standardized procedure, test compounds were compared in their ability to stimulate the shaking response by intravenous injection into a cannulated femoral vein, by perioral administration, and by topical delivery to the abdominal skin.

Intravenous.

FIG. 5B shows shaking frequency of pentobarbital-anesthetized male rats after intravenous [i.v.] injection of 2 mg/kg of test compounds. Each rat was given two injections with a 30 min interval. The graph shows the $2^{nd}$ trial data. Shaking frequency was counted for 15 min after injection. Shaking was observed immediately after i.v. injection and at least 78% of the total shakes occurred in the first 5 min after injection. The response in the second trial was at least as robust in the first trial, showing the lack of desensitization.

Note the low frequency shaking observed with intravenous DIPA-1-8, DIPA-1-9 and DAPA-2-8 despite high relative potency on TRPM8 $EC_{50}$. Shaking frequency is an undesirable drug effect because it means that if it occurs, the drug is being absorbed into the systemic circulation and will cause "chills". It is preferable to have a localized drug action on the colon mucosa. Thus, DIPA-1-8, DIPA-1-9 and DAPA-2-8 are preferred embodiments, together with DAPA-2-5. The total number of carbons in these embodiments is 13 to 16 carbons. It is recognized that further synthesis of Dapa with up to 20 carbons can result in analogs that retain TRPM8 potency, yet remain localized when applied to the colon mucosa. A higher number of carbons will result in a "waxy solid" that will be difficult to dissolve and deliver.

Perioral.

Test compounds were dissolved in saline and administered by oral gavage to pentobarbital-anesthetized male albino rats at 20 mg/kg at a volume of 0.1 mL/100 g body weight [N=3 to 4 rats per compound]. Shaking was counted over a 40 min period and recorded at 10-min intervals. The results are shown in FIG. 5C.

FIG. 5C shows shaking frequency of pentobarbital-anesthetized male rats after perioral administration of Dapa, dissolved in saline, at 20 mg/kg with a gavage needle. Shaking frequency was counted for 40 min. The surprising lack of activity in the di-sec-butyl-analogs (DAPA-2-x) is noted. Three of the four "diisopropyl" compounds caused vigorous shaking. The "di-sec-butyl" compounds were relatively inactive, except DAPA-2-5 which elicited an average of 4 shakes in the 40 min observation period. By contrast, DIPA-1-5, DIPA-1-6, and DIPA-1-7 produced an average shaking frequency of 86, 56, and 36 shakes, respectively. It is possible that its smaller molecular size facilitates absorption and allows greater access to systemic receptors, and therefore more shaking.

Topical.

For topical application of DAPA, the abdominal skin of the anesthetized rat was shaved and 20 μL of the pure DAPA was applied with a micropipette onto a ~1 cm diameter circle of skin, enclosed with a ring of cream [Baby cream "Nevskaya kosmetika Detskyi" Nevskaya Kosmetika Inc., Saint-Petersburg 192029], as shown in FIG. 5D. The number of shakes was counted for 1 hr after application.

FIG. 5D shows shaking frequency of pentobarbital-anesthetized male rats after 20 μL of the pure test compounds was delivered onto the abdominal skin. Test substances were applied with a micropipette to the center of a circle enclosed by cream on the shaved skin, as shown in the cartoon insert on the graph. The surprising lack of activity in the di-sec-butyl-analogs (DAPA-2-x) after transdermal delivery is noted. The surprising potency of DIPA-1-5 and DIPA-1-6 was unexpected but similar to what was seen with perioral administration. These smaller may penetrate faster through the skin barrier and go into the systemic circulation.

Analysis of $EC_{50}$ and Shaking after Perioral, Topical and Intravenous Delivery The pattern of Dapa bioactivity for the three routes of administration provides an excellent framework and rationale for the selection of the best API for LGIT dysfunction.

The less potent TRPM8 analogs, namely, 1-5, 1-6, 2-4 and 1-10 were judged to be not suitable because of a lack of activation power on TRPM8.

The perioral and topical shaking seen with 1-5, 1-6 and DIPA-1-7 made these candidates less attractive for oral or rectal delivery because shaking is associated with strong sensory stimuli, and this is not desirable if the molecule is absorbed from the LGIT mucosa into the systemic circulation.

DIPA-1-8, DIPA-1-9, DAPA-2-5, DAPA-2-6, DAPA-2-7, and DAPA-2-8 did not produce shaking after perioral and topical administration. These analogs are thereby more attractive because these results indicate that these analogs remain localized in tissues after topical delivery and they also have good TRPM8 potency.

The greater shaking frequency see with intravenous DAPA-2-6 and DAPA-2-7 versus DIPA-1-8 and DIPA-1-9 meant that these molecules produced stronger sensations of cold, an effect which made them somewhat less desirable than DIPA-1-8 and DIPA-1-9 because of the risks of systemic absorption.

From this analysis of the data, namely, TRPM8 $EC_{50}$ and perioral, topical, and intravenous shaking activity, the rank order for the best selection of an API would be DIPA-1-9>DIPA-1-8> followed by DAPA2-8, DAPA-2-5, DAPA-2-6 and DAPA-2-7. DIPA-1-9 is especially attractive because it does not cause shaking, and yet it is potent on the TRPM8 receptor.

TABLE 4

Shaking frequency after perioral [per 20 mg/kg body weight] or topical delivery of 20 μl test compounds [per animal] to the anesthetized rat.

| Code | Mol Wt | # Cs | ×Menthol | Perioral | Topical | Intravenous |
|---|---|---|---|---|---|---|
| DIPA-1-5 | 204 | 11 | 0.7 | 86 ± 7 | 138 ± 15 | 19 ± 3 |
| DIPA-1-6 | 218 | 12 | 1.6 | 56 ± 5 | 69 ± 8 | 39 ± 4 |
| DIPA-1-7 | 232 | 13 | 5.4 | 36 ± 4 | 79 ± 8 | 25 ± 3 |
| DIPA-1-8 | 246 | 14 | 5.4 | 0 | 7 ± 2 | 14 ± 2 |
| DIPA-1-9 | 260 | 15 | 4.0 | 0 | 0 | 3 ± 1 |
| DAPA-2-4 | 218 | 12 | 0.3 | 0 | 0 | 8 ± 2 |
| DAPA-2-5 | 232 | 13 | 2.2 | 4 ± 1 | 0 | 20 ± 2 |
| DAPA-2-6 | 246 | 14 | 4.7 | 0 | 0 | 30 ± 3 |
| DAPA-2-7 | 260 | 15 | 3.4 | 0 | 0 | 15 ± 2 |
| DAPA-2-8 | 274 | 16 | 2.9 | 0 | 0 | 2. |

Study 8

Formulation of Dapa for Enteric Coated Tablet or Capsule.

The DAPA molecules are colorless or pale yellow liquids with a hydrophilic center attached to three hydrophobic alkyl chains, and thus create an unusual molecular environment for bonding to tablet excipients. Nobody has yet tried to create an enteric tablets with the DAPA compounds of this discovery. In this discovery, an excipient of special interest is magnesium aluminometasilicate.

Three Preparations were Made and Labeled as ODT-A, ODT-B, and ODT-C.

ODT-A was prepared by dissolving the DAPA compound in absolute ethanol, adding a 80% mannitol-20% maltitol mixture of equal weight and then adding an equal volume of distilled water. The mixture was the stirred with a glass rod, and dispensed onto a piece of wax or parchment paper with a disposable plastic pipette. The viscous liquid drop formed was then dried under a heat source for at least 4 hr. The nominal dose of the API in ODT-A ranged from 1 to 3 mg/tablet. The dried tablets weighed on average 150 mg each and when on the dorsal surface of the tongue, rapidly dissolved completely in saliva and coated the oropharyngeal surface. These tablets were suitable for initial pilot studies, but were not uniform in size, were friable, especially in conditions of high ambient humidity, and were not readily amenable to further analytical evaluation.

ODT-B was prepared by expert consultants at Formurex, Inc., 2470 N. Wilcox Road, Stockton, Calif. 95215. Tel: (209) 931 2040, under the supervision of Ravi Mahalingam, Ph.D. and Rajendra S. Tandale, Ph.D. This study is summarized in a report [FR-2013-1038, May 1, 2013, Formulation of DAPA-2-5 into Upper Esophageal/Lower Pharynx Dosage Forms] incorporated here by reference. The experimental objectives were to develop prototype tablet formulations to deliver DAPA-2-5 at 1.5, 2.0, 5.0 and 8.0 mg doses, to characterize tablet properties, and to develop an HPLC method for quantifying release of DAPA-2-5.

Experimental Procedures

These materials, sources/Lot# were used: DAPA-2-5, Phoenix Pharmaceuticals, Inc. Lot #429773; Co-Processed Lactose, povidone and crospovidone (Ludipress), J. T. Baker Lot #1AH0516; Microcrystalline cellulose, NF (Avicel PH102), FMC Biopolymer Lot # P212824001; Co-Processed microcrystalline cellulose and guar gum (Avicel CE-15), FMC Biopolymer Lot # RH1082185; Povidone, USP (Plasdone K-29/32), ISP Technologies Lot #05100280713; Xanthan Gum, USP/NF (Xanthural 75). CP Kelco, Lot #2B4685K; Mannitol, USP (Mannogem), SPI Pharma, Lot #12000076G; Co-Processed ODT Excipient (F Melt), Fuji Chemical Ind. Co., Lot #201002; Maltodextrin NF altrin M510), Grain Processing Corporation, Lot # M0832960; Colloidal Silicon Dioxide (Cab-O-Sil M5P), Cabot, Lot #1222272; Aluminum Magnesium Metasilicate, USP (Neusilin US2), Fuji Chemical Ind. Co. Lot #009025; Co-processed ODT Excipient (Pharmaburst 500), SPI Pharma Lot #10M019; Co-processed Lactose (Ludipress), BASF Lot #17137275L0; Hypromellose, USP, 50 mPa·S, Spectrum Chemicals Lot #2610277; Magnesium stearate, NF (HyQual)m Mallinckrodt Lot #20100125.

The pre-blended excipients supplied by manufacturers are generally bulking agents or diluents and sugars such as mannitol, lactose, or maltitol. Other excipients are microcrystalline cellulose, starch, colloidal silicon dioxide, sodium starch glycolate, and the lubricants are magnesium or calcium stearate. The study was conducted in three stages the DAPA Active Pharmacological Ingredient [API] was converted into a solid form by dilution with a pre-blended excipient, by 1) Dilution Approach, 2) Adsorption, or 3) Incorporation into mucoadhesive polymers.

Dilution Approach: DAPA-2-5 liquid were loaded onto excipients (batch size: 12-24 g) in ~12 experiments. The API and the selected excipients were mixed geometrically using a stainless steel spatula, and the mixture passed through sieve #20. The sieved blend was lubricated using magnesium stearate (previously sieved through mesh #40), and evaluated for appearance and flow property (through funnel). Based on the flow nature, selected blends were compressed in to tablets using Ø7.2 mm (for 120 mg tablets) or Ø9.5 mm (for higher than 120 mg tablet) standard concave round tooling on an Acura rotary press. Tablets were evaluated for thickness, hardness, friability, and disintegration test in 10 mL of purified water at room temperature. The appearance of powder blends and tablets were photographed.

The excipients: Ludipress, Avicel PH 102, Avicel CE-15, Mannitol, F-Melt, and Maltodextrin, yielded blends that were oily in appearance and had poor flow. The exception was Pharmaburst 500 blends. However, Pharmaburst 500 blends showed poor compressibility and varying the amount of Pharmaburst 500 did not enhance compressibility. Further tests were done with two silicate excipients: Neusilin US2, and Syloid 244FP. Surprisingly, Neusilin US2 was an effective excipient for blending with DAPA-2-5. Subsequent mixing with Pharmaburst yielded blends that could be compressed into tablets with acceptable physical properties of hardness, friability, and disintegration times. Various mucoadhesive polymers were tried and the results suggested that incorporation of hypromellose may have beneficial effects.

The formed tablet was evaluated by several parameters. The dissolution rate is the time for the tablet to dissolve in a fixed volume of water [e.g. 10 mL] and, in the case of the ODT, the disintegration time should be less than 30 sec. Tablet hardness measures the structural integrity of a tablet "under conditions of storage, transportation, and handling before usage". Force is applied to the tablet until it breaks, and the unit of force can be in Newtons or a Kilopond (kp). The Newton unit is given by the equation 1 Newton=1 kg·m/s$^2$ where kg is kilogram, m is meter, and s is second. Friability, or being friable, describes the ability of a solid substance to break up to smaller pieces with little effort. A typical index of friability is the % of the tablet that is chipped off after mechanical stress.

The final preblend for ODT-B that might be optimal for clinical trials for a 100 mg ODT was a mix of DAPA-2-5: 1.5 mg, Neusilin US2: 20.0 mg, Blend: Pharmaburst 500 76.5 mg, Hypromellose [50 cps] 1.0 mg, and Mg-stearate: 1.0 mg, to give a non-oily free flowing powder that can be put into the funnel of a tablet making machine to yield tablets of Thickness (mm): 3.4, Hardness (kp): 3.0-5.0, Friability (% w/w): 0.04, Disintegration time (Sec): <20, and good Compressibility.

A high pressure liquid chromatography [HPLC] method was developed for analysis of DAPA-2-5 in aqueous solution. The chromatographic conditions were: Column: Waters XTerra RP18, 150×4.6 mm, 3.5 µm, Column temperature: 40° C., Mobile phase: 0.1% Tetrabutyl ammonium and Tri fluro acetic acid in 900 mL water and 100 mL Acetonitrile, Flow: 1.0 ml/min, Diluent: Water, Wavelength: 226 nm, Injection Volume: 100 µL, Run time: 10 min, Standard Preparation: 0.75 mg/mL of DAPA-2-5 in water. Sample Preparation: Equivalent to 0.75 mg/mL of DAPA-2-5 in water. Prototype tablets containing DAPA-2-5 were disintegrated and the content of DAPA-2-5 measured. The results showed that 86±2% of DAPA-2-5 was recovered from the aqueous phase and thus available for bioactivity. It is likely that the non-eluted DAPA-2-5 remains tightly bound to sites on the Neusilin US2.

From these experiments, it was concluded that a mineral excipient such as Neusilin US2 will be an excellent excipient for Dapa. Examples of recipes for blending Dapa with Neusilin and other excipients are described below.

a. a DAPA compound dissolved in an equal part of ethanol by volume, and then an 1.5 to 2.0 part by weight of Neusilin US2 is added, the combination mixed, and the ethanol is evaporated by placing the mixture under a heat source, e.g. a 100 watt light bulb. For example, to 1.5 g of DAPA-2-5 is added 1.5 g of absolute ethanol, followed by 2.0 g of Neusilin US2. The mixture is shaken or mixed in a Speedmixer at 500 rpm for 1 min. The sample is placed under a heat source and about 2 hr later, the sample size is re-weighed with the expectation that the ethanol has been evaporated and the sample now weights 3.5 g. This powder is free-flowing.

b. a sample of maltitol powder is prepared (Maltisorb® P200 from Roquette).

c. a sample of Prosolv® EasyTab is prepared (JRS Pharma, Rosenburg, Germany).

d. a blend of a. [2.80 g], b. [15.73 g] and c. [31.46 g] is prepared to make 1000 ODT tablets, each weighing 50 mg and containing 1.2 mg of DAPA-2-5.

e. the blend is first shaken by hand, then placed for 2 min in a SpeedMixer at 500 rpm. The blend is poured into the funnel of a New Single Punch Tablet Press Pill Making Machine Maker TDP-1-5 [available from Amazon.com] and the extruded tablets are collected.

A second inorganic excipient, CaHPO$_4$, Spray Dried Granule, Dibasic Calcium Phosphate Anhydrous; Calcium Hydrogen Phosphate, Anhydrous, trade name Fujicalin®, made by by Fuji Chemical Co., Ltd., was also found to be an effective adsorption ingredient for the DAPA compounds prior to blending with pre-mixed blends. The adsorption capacity was, however, half of Neusilin US2 and disintegration rate was twice as long.

In summary, prototype formulations of DAPA compounds were created. The tablets were designed for delivery of the API onto the surfaces of the upper digestive tract, but the same principles have value for the lower digestive tract. The granulation process was aimed at choosing the right parameters for a powder blend that will be free-flowing, compactable to certain hardness, and have minimal friability, and fast disintegration time. It was discovered that a key ingredient in successful formulation was the use of aluminum metasilicate oxide, commercially available as Neusilin US2. This excipient allowed the liquid DAPA compounds to be formulated into a tablet that met standard criteria for use. A representative formulation was composed of, DAPA-2-5 (I.5%), Neusilin US2 (20.0%), Pharmaburst 500 (76.5%), Hypromellose (1.0%), and Magnesium stearate (1.0%). An alternative pre-blend excipient to Pharmaburst 500 was EasySolv. These blends have excellent properties for compression into an enteric tablet or to be put inside a capsule for delivery to the lower bowel lumen.

Study 9

Toxicity

Preliminary toxicological studies were conducted on DAPA-2-5 and DAPA-2-7. Neither of these compounds was mutagenic in the Ames test (Strains TA 98 and TA100, with and without liver activation) (tests conducted by Apredica, Watertown, Mass., USA).

DAPA-2-7, dissolved in 3% ethanol/97% 1,2-propanediol, or vehicle alone, was administered subcutaneously to male rats (N=8 per group) at 30 mg/kg body weight daily for 7 days, and on the 8th day, the animals were euthanized with sodium pentobarbital and the major organs (body, heart, liver, lungs, kidney, testes, brain) were removed and weighed. Heart tissues (ventricle and heart valves) and liver samples were stained with hematoxylin and eosin and the histology examined. There were no significant differences in body or organ weights between the two groups and the heart and liver histology were normal.

A study with an identical design, but with DAPA-2-5, administered at 20 mg/kg perioral by gavage for 7 days (N=10 per group), gave similar results. In a large scale trial, DAPA-2-5 was administered via drinking water to male rats for 40 days. The DAPA-2-5 was mixed with condensed milk [8.5%] at 0.5 mg/mL and liquid consumption was monitored. The averaged intake in the treated group [N=12 rats] was 41 mg/kg body weight/day for 40 days. The vehicle alone group was N=11. In both experiments there were no statistical difference in organ weights or in histology between groups treated with DAPA-2-5 and groups treated with vehicle. These studies show that Dapa is relatively free of adverse effects and have the potential to be used as pharmaceuticals.

The invention claimed is:

1. A method of treatment of intestinal muscle spasms and of intestinal mucosa inflammation in a human subject with lower gastrointestinal tract dysfunction and in need of treatment thereof, comprising:
    providing a composition, the composition having a therapeutically effective amount of a compound selected from the group consisting of 1-[Diisopropyl-phosphinoyl]-octane [DIPA-1-8], 1-[Diisopropyl-phosphinoyl]-nonane [DIPA-1-9], 1-[Di-sec-butyl-phosphinoyl]-pentane [DAPA-2-5], 1-[Di-sec-butyl-phosphinoyl]-pentane [DAPA-2-8] and combinations thereof and
    a delivery agent carrying the compound, the delivery agent adapted for topical release of the compound to the intestinal musosa; and, administering said composition to the subject.

2. The method as in claim 1 wherein the compound is 1-[Diisopropyl-phosphinoyl]-octane [DIPA-1-8].

3. The method as in claim 1 wherein the compound is 1-[Diisopropyl-phosphinoyl]-nonane [DIPA-1-9].

4. The method as in claim 1 wherein the compound is 1-[Di-sec-butyl-phosphinoyl]-pentane [DAPA-2-5].

5. The method as in claim 1 wherein the compound is 1-[Di-sec-butyl-phosphinoyl]-pentane [DAPA-2-8].

6. The method as in claim 1 wherein the delivery agent is a controlled release tablet or capsule for oral intake.

7. The method as in claim 1 wherein the delivery agent is a suppository for rectal administration.

8. The method as in claim 1 wherein the deliverable amount of the compound to the intestinal musosa is 5 to 200 mg per unit dose.

9. The method as in claim 1 wherein the lower gastrointestinal tract dysfunction is caused by irritable bowel syndrome.

10. The method as in claim 1 wherein the lower gastrointestinal tract dysfunction is caused by inflammatory bowel disease.

11. The method as in claim 1 wherein the delivery agent is an enteric coated tablet or capsule which includes a mineral excipient adapted to deliver the active agent to the intestinal musosa when ingested.

12. The method as in claim 11 wherein the tablet or capsule has from 2 to 20 wt. % of the mineral excipient.

13. The method as in claim 11 wherein the mineral excipient is magnesium aluminometasilicate represented by the empirical formula $Al_2O_3 \cdot MgO \cdot 2SiO_2 \cdot xH_2O$.

14. The method as in claim 11 wherein the mineral excipient is CaHPO4, Spray Dried Granule, Dibasic Calcium Phosphate Anhydrous; Calcium Hydrogen Phosphate, Anhydrous.

* * * * *